United States Patent [19]

Schefczik

[11] Patent Number: 5,047,570

[45] Date of Patent: Sep. 10, 1991

[54] PREPARATION OF 2-CYANO-3-AMINOACRYLONITRILE DERIVATIVES

[75] Inventor: Ernst Schefczik, Ludwigshafen, Fed. Rep. of Germany

[73] Assignee: BASF Aktiengesellschaft, Ludwigshafen, Fed. Rep. of Germany

[21] Appl. No.: 308,617

[22] Filed: Feb. 10, 1989

[30] Foreign Application Priority Data

Feb. 12, 1988 [DE] Fed. Rep. of Germany ....... 3804394

[51] Int. Cl.$^5$ ........................................... C07C 253/30
[52] U.S. Cl. .................................. 558/375; 544/163; 544/208; 544/224; 544/241; 544/402; 546/230; 546/330; 548/437; 548/477; 548/550; 548/578; 549/74
[58] Field of Search ................ 558/375; 544/163, 208, 544/224, 241, 402; 546/230, 330; 548/437, 477, 550, 578; 549/74

[56] References Cited

U.S. PATENT DOCUMENTS

| | | | |
|---|---|---|---|
| 3,116,319 | 12/1963 | Creighton et al. | 558/375 |
| 3,694,484 | 9/1972 | Cresswell et al. | 558/375 |
| 4,540,791 | 9/1985 | Cassar et al. | 558/375 X |
| 4,667,051 | 5/1987 | Schefczik | 558/375 |

FOREIGN PATENT DOCUMENTS 2434922 1/1975 Fed. Rep. of Germany .
1200445 7/1970 United Kingdom ................ 558/375
1275882 5/1972 United Kingdom .

OTHER PUBLICATIONS

Baddiley et al.; J. Chem. Soc. (1943), pp. 386–387.
Patent Abstracts of Japan, unexamined applications, C Field, Band 6, Nr. 139; Jul. 28, 1982.
J. Chem. Soc. (1943), pp. 388–390; Kenner et al.
Synthesis (1981), pp. 130–133; Celerier et al.
Dyes and Pigments 3 (1982), pp. 81–121; Weaver et al.

Primary Examiner—Joseph Paul Brust
Attorney, Agent, or Firm—Oblon, Spivak, McClelland, Maier & Neustadt

[57] ABSTRACT

3-Amino-2-cyanoacrylonitrile derivatives of the formula

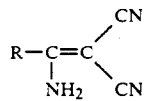

where R is substituted $C_1$–$C_{10}$-alkyl, substituted or unsubstituted styryl, substituted or unsubstituted phenyl or aromatic heterocyclyl, are prepared by treating a nitrile in an inert organic diluent at from 0° to +30° C. with a substituted or unsubstituted $C_1$–$C_6$-alkanol in the presence of a hydrogen halide and reacting the resulting iminoester hydrohalide directly or after isolation with malodinitrile in an inert organic diluent at from 20° to 100° C. in the presence of a base.

4 Claims, No Drawings

PREPARATION OF 2-CYANO-3-AMINOACRYLONITRILE DERIVATIVES

The present invention relates to a novel process for preparing 2-cyano-3-aminoacrylonitrile derivatives by treating nitriles with an alkanol in the presence of a hydrogen halide and reacting the resulting iminoester hydrohalide with malodinitrile in the presence of a base.

DE-A-2,434,922 discloses the preparation of 2-cyano-3-aminoacrylonitrile derivatives. However, the synthesis route used there is complicated since it proceeds via several stages. In addition, the carboxylic anhydrides required as starting components are only accessible to a limited degree.

Synthesis 1981, 130, describes the reaction of various iminoester hydrochlorides with Meldrum acid (2,3-dimethyl-1,3-dioxan-4,6-dione). It is also mentioned there that the hydrochloride of methyl acetimidate reacts with malodinitrile under basic conditions. At the same time, however, it is pointed out that good yields are obtained if the reaction is carried out with Meldrum acid. In addition, no information is provided about the reaction product with malodinitrile. J. Chem. Soc. 1943, 388, further discloses in this context that the reaction of forminino ether with malodinitrile gives 4-amino-5-cyanopyrimidine.

It is an object of the present invention to provide a novel process which makes it possible to prepare 2-cyano-3-aminoacrylonitrile derivatives by a simple synthesis route from starting materials which should be readily accessible.

We have found that this object is achieved with the preparation of 3-amino-2-cyanoacrylonitrile derivatives of the formula I

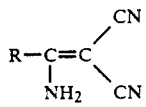  (I)

where R is substituted $C_1$-$C_{10}$-alkyl, substituted or unsubstituted styryl, substituted or unsubstituted phenyl or aromatic heterocyclyl by treating a nitrile of the formula II

R—CN  (II)

where R is as defined above, in an inert organic diluent at from 0° to +30° C. with a substituted or unsubstituted $C_1$-$C_6$-alkanol in the presence of a hydrogen halide and reacting the resulting iminoester hydrohalide of the formula III

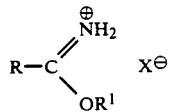

where R is as defined above, $R^1$ is substituted or unsubstituted $C_1$-$C_6$-alkyl and $X^\ominus$ is a halide ion, with or without intermediary isolation, with malodinitrile in an inert organic diluent at from 20° to 100° C. in the presence of a base.

All the alkyls appearing in the abovementioned formulae can be not only straight-chain but also branched.

Substituted $C_1$-$C_{10}$-alkyl R is derived for example from the following radicals: methyl, ethyl, propyl, isopropyl, butyl, isobutyl, sec.-butyl, tert.-butyl, pentyl, isopentyl, neopentyl, tert.-pentyl, hexyl, heptyl, octyl, 2-ethylhexyl, nonyl or decyl.

Suitable substituents for $C_1$-$C_{10}$-alkyl are for example $C_1$-$C_4$-alkoxy, phenoxy, phenyl which may be substituted by $C_1$-$C_4$-alkyl, nitro, halogen, in particular fluorine, chlorine or bromine, hydroxyl or $C_1$-$C_4$-alkoxy, $C_1$-$C_4$-monoalkyl- or -dialkyl-carbamoyl, pyrrolidinocarbonyl, piperidinocarbonyl, morpholinocarbonyl, piperazinocarbonyl, N-($C_1$-$C_4$-alkyl)-piperazinocarbonyl, phenylthio, phenylsulfonyl, anilino, $C_1$-$C_4$alkanoylamino, benzoylamino, N-($C_1$-$C_4$-alkyl)-N-($C_1$-$C_4$-alkanoyl)-amino, N-($C_5$-$C_7$-cycloalkyl)-N-($C_1$-$C_4$-alkanoyl)-amino, N-($C_1$-$C_4$-alkyl)-N-benzoylamino, N-phenyl-N-benzoylamino, phenylsulfonylamino, N-($C_1$-$C_4$-alkyl)-N-phenylsulfonylamino, N-phenyl-N-phenylsulfonylamino, N,N'-($C_1$-$C_4$-dialkyl)ureido, N-phenyl-N'-($C_1$-$C_4$-alkyl)ureido, N,N'-diphenylureido, 4,5-dichloropyridazin-1-yl or a radical of the formula

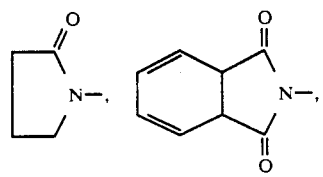

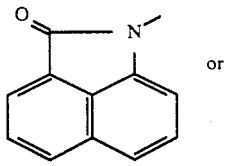 or

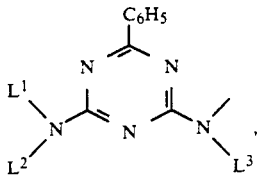

where $L^1$, $L^2$ and $L^3$ are identical or different and each is independently of the others hydrogen or $C^1$-$C^4$-alkyl.

R is further for example unsubstituted phenyl, phenyl which is substituted by $C_1$-$C_4$-alkyl, $C_1$-$C_4$-alkoxy, halogen, in particular fluorine, chlorine or bromine, hydroxyl, phenoxy, phenylthio, phenylsulfonyl, $C_1$-$C_4$-alkoxycarbonyl, $C_1$-$C_4$-hydroxyalkyl, $C_1$-$C_4$-haloalkyl, $C_1$-$C_4$-(pyrrolidino)-, -(piperidino)-, morpholino)-, -(piperazino)- or -[N-($C_1$-$C_4$-alkyl)piperazino]-alkyl, $C_1$-$C_4$-phenylalkoxy, $C_1$-$C_4$-dialkylsulfamoyl or $C_1$-$C_4$-alkanoylamino, styryl, styryl which is substituted by $C_1$-$C_4$-dialkylamino, pyridinyl, pyridinyl which is substituted by $C_1$-$C_4$-alkyl, thienyl or thienyl which is substituted by $C_1$-$C_4$-alkyl.

A preferred form of the process according to the invention comprises using nitriles of the formula II where R is 3-($C_1$-$C_4$-alkoxy)propyl, benzyl or phenyl.

Suitable $C_1$-$C_6$-alkanols are for example methanol, ethanol, propanol, isopropanol, butanol, isobutanol, sec.-butanol, pentanol, isopentanol, neopentanol or hexanol. An example of a substituted or unsubstituted $C_1$–$C_6$-alkanol is 2-chloroethanol. The use of methanol, ethanol or propanol is preferred.

A suitable hydrogen halide is for example hydrogen fluoride, hydrogen chloride or hydrogen bromide. The use of hydrogen chloride is preferred.

Inert organic diluents which can be used in the process according to the invention are for example hydrocarbons which may be halogenated or in particular chlorinated, such as toluene, xylene, chloroform, 1,1,1-trichloroethane, 1,2-dichloroethene, 1,2-dichloroethane, chlorobenzene or 1,2-dichlorobenzene, or ethers, such as diethyl ether, methyl tert.-butyl ether, tetrahydrofuran or dioxane.

It is also possible to use alkanols, for example methanol or ethanol, as diluents. In this case the alcohol simultaneously serves as reactant and diluent.

Suitable bases for the novel process are for example inorganic bases, such as sodium carbonate, potassium carbonate, sodium bicarbonate or potassium bicarbonate, or organic bases, for example tertiary amines, such as triethylamine, tripropylamine, triisopropylamine, tributylamine, N,N-dimethylaniline or N,N-diethylaniline, or alkali metal alkoxides, such as sodium methoxide or sodium ethoxide.

The process according to the invention is conveniently carried out by initially introducing nitrile II and $C_1$–$C_6$-alkanol in a molar ratio of from 1:1 to 1:5, preferably of from 1:1 to 1:2, together with the inert diluent and passing into this mixture with stirring from 1 to 5 moles, preferably from 1 to 2 moles, of hydrogen halide at from 0° to +30° C. Following a reaction time of from about 2 hours to 20 hours the resulting iminoester hydrohalide III is reacted directly or after an intermediate isolation with malodinitrile.

The iminoester hydrohalide III is present, depending on the nature of the inert diluent, either in a solid state or as a solution. In some cases it can be of advantage to isolate the iminoester hydrohalide III prior to its reaction with malodinitrile. If it is to be isolated first, it is either filtered off with suction or stripped of diluent under reduced pressure.

A preferred procedure comprises directly reacting the iminoester hydrohalide III further without intermediate isolation. To this end, the reaction mixture is admixed either first with the malodinitrile and then with the base or preferably first with the base and then with the malodinitrile.

The amounts used per mole of nitrile II are from 1 to 2 moles, preferably from 1 to 1.1 moles, of malodinitrile and from 1 to 2 moles, preferably from 1 to 1.2 moles, of base.

If the iminoester hydrohalide III has been isolated first, it is initially again admixed with an inert organic diluent and then, as described above, with malodinitrile and base.

The reaction mixture is then heated with stirring to from 20° to 100° C., preferably to from 20° to 80° C., and left at that temperature for from 1 to 10 hours. Care must be taken to ensure that this reaction step takes place in a neutral or alkaline medium.

If the inert diluent is miscible with water, the reaction mixture, after it has cooled down, is diluted with water, and the target product I precipitates. If the diluent is water-immiscible, it is advisable to remove the diluent by steam distillation.

The 2-cyano-3-aminoacrylonitrile derivative thus obtained may after drying be used directly for further syntheses or be further purified in a conventional manner.

The advantages of the novel process, which can be carried out not only continuously but also batchwise, are that the target products of the formula I are obtained in a simple manner and in good yield and high purity. In addition, the novel process is very versatile, since the starting nitriles of the formula II are generally readily accessible.

The 2-cyano-3-aminoacrylonitrile derivatives of the formula I prepared by means of the process according to the invention are useful intermediates for the synthesis of dyes, drugs or crop protection agents.

For instance, they may be converted in a conventional manner, as described in DE-A-2,434,922, with hydrogen halide into the corresponding 2-cyano-3-aminoacrylic thioamide derivatives of the formula IV

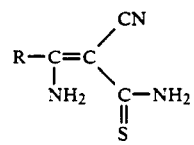

where R is as defined above, which in turn may be converted in a conventional manner, as described in DE-A2,434,922, by oxidative cyclization, for example with aqueous hydrogen peroxide solution, into isothiazoles of the formula V

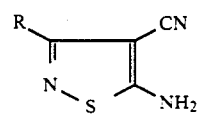

(V)

where R is as defined above. The isothiazoles V are useful diazo components for azo dyes (see for example Dyes and Pigments 3 (1982), 106).

The Examples which follow illustrate the invention in more detail.

EXAMPLE 1

140 g of gaseous hydrogen chloride were passed at from 5° to 10° C. into a solution of 206 g of benzonitrile and 128 g of methanol in 500 ml of toluene. The mixture was subsequently stirred at room temperature for 16 hours, and excess hydrogen chloride was then removed under reduced pressure in the course of 4 hours. 300 g of methanol were then added, followed by 240 g of triethylamine at up to a pH of from 7.5 to 8, with cooling to from 10° to 20° C. 132 g of malodinitrile were added, the mixture was then refluxed for 2 hours and then admixed with 400 ml of water, and the toluene was distilled off with steam. After cooling down, the crystallized product was filtered off with suction and washed with water. Drying left 315 g of 2-cyano-3-amino-3-phenylacrylonitrile having a melting point of from 182° to 183° C. (from ethanol).

| | Analysis: $C_{10}H_7N_3$ (169) | | |
|---|---|---|---|
| calculated: | C 71.0 | H 4.2 | N 24.8 |
| found: | 71.1 | 4.3 | 25.0 |

EXAMPLE 2

Example 2 was carried out similarly to Example 1, except that the iminoester hydrochloride was isolated by filtration with suction.

132 g of malodinitrile were then dissolved in 500 ml of methanol. 343 g of methyl benzoimidate hydrochloride were then added with stirring at from 10° to 20° C., followed by 205 g of triethylamine added dropwise. The mixture was then refluxed for 4 hours, and the methanol was distilled off with steam. After cooling down, the suspended crystals were filtered off with suction, washed with water and dried, leaving 337 g of 2-cyano-3-amino-3-phenylacrylonitrile (identical to the compound obtained in Example 1).

EXAMPLE 3

103 g of benzonitrile were mixed with 64 g of methanol, and gaseous hydrogen chloride wase introduced at from 10° to 15° C. until the weight increase was 70 g. The reaction was continued with stirring at room temperature for 16 hours, and excess hydrogen chloride and methanol were then removed under reduced pressure. The salt paste residue was made to dissolve with 300 ml of methanol and rendered alkaline by the dropwise addition of 190 g of 30% strength by weight methanolic sodium methoxide solution at from 10° to 20° C. 66 g of malodinitrile were then added, and the mixture was stirred at from 50° to 60° C. for 4 hours. During cooling down the reaction mixture was diluted with 1,000 ml of water and then brought to a neutral pH by addition of hydrochloric acid. The precipitate formed was filtered off with suction, washed with water and dried to leave 151 g of 2-cyano-3-amino-3-phenylacrylonitrile having the properties described in Example 1.

(Instead of sodium methoxide it is also possible to use sodium carbonate or potassium carbonate.)

EXAMPLE 4

90 g of gaseous hydrogen chloride were passed at from 5° to 10° C. into a mixture of 880 ml of chloroform, 234 g of benzyl cyanide and 65 g of methanol. The mixture was then left to stand at 10° C. for 12 hours, and dry nitrogen was then blown through the reaction mixture for several hours to remove excess hydrogen chloride. 280 g of triethylamine were then added dropwise at from 10° to 20° C., followed by 132 g of malodinitrile. The mixture was then refluxed for 6 hours, and thereafter the chloroform was distilled off with steam. The result was an aqueous solution which on cooling shed crystals. The solution was diluted with the same volume of cold water, and the crystals were filtered off with suction and washed with water. Drying left 353 g of 2-cyano-3-amino-3-benzylacrylonitrile in the form of colorless crystals. A sample recrystallized from ethanol has a melting point of from 162° to 163° C. and gives the following analysis:

|  | $C_{11}H_9N_3$ (183) | | |
| --- | --- | --- | --- |
| calculated: | C 72.1 | H 5.0 | N 22.9 |
| found: | 72.0 | 5.0 | 22.8 |

EXAMPLE 5

Gaseous hydrogen chloride was passed into a stirred mixture of 100 ml of dioxane, 32 g of methanol and 151.5 g of 2-chlorobenzyl cyanide at from 10° to 15° C. until the weight increase was 50 g. The reaction mixture was subsequently stirred at room temperature for 16 hours, and excess hydrogen chloride was then removed under reduced pressure. A solution of 66 g of malodinitrile in 200 ml of methanol was then poured into the resulting mass of crystals, the mixture was cooled, and 125 g of triethylamine were then added dropwise at from 15° to 20° C. The reaction mixture was then heated at the boil for 4 hours before being dissolved into 1,000 ml of water. Filtering with suction and drying left 214 g of the compound of the formula

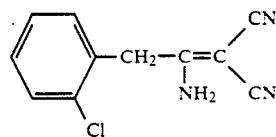

having a melting point of from 162° to 163° C. (from ethanol). (Cl calculated 16.3 found 16.3)

The Table below contains further 2-cyano-3-aminoacrylonitriles of the formula

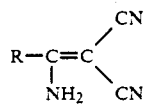

which were obtained in a similar manner.

| Example | R | prepared acc. to Example | mp [°C.] (solvent of the recrystallization) |
| --- | --- | --- | --- |
| 6 | CH₃—⌬— | 1 | 150–151 (pentanol) |
| 7 | ⌬— (CH₃ meta) | 2 | 188–189 (pentanol) |

-continued

| Example | R | prepared acc. to Example | mp [°C.] (solvent of the recrystallization) |
|---|---|---|---|
| 8 | 4-Cl-C₆H₄- | 1 | 224–225 (chlorobenzene) |
| 9 | 4-HO-C₆H₄- | 1 | 268–269 (pentanol) |
| 10 | 4-CH₃O-C₆H₄- | 2 | 193–194 (chlorobenzene) |
| 11 | 4-(C₆H₅—CH₂O)-C₆H₄- | 1 | 173–174 (ethanol) |
| 12 | 4-(CH₃)₃C-C₆H₄- | 3 | 154–155 (xylene) |
| 13 | 4-(C₂H₅OOC)-C₆H₄- | 1 | 170–171 (ethanol) |
| 14 | 3-(COOC₂H₅)-C₆H₄- | 1 | 163–164 (ethanol) |
| 15 | 4-(morpholino-CH₂)-C₆H₄- | 1 | 184–185 (propanol) |
| 16 | 4-(HOCH₂)-C₆H₄- | 1 | 241–242 (acetic acid) |
| 17 | 4-(ClCH₂)-C₆H₄- | 1 | 143–144 (ethanol) |
| 18 | 4-(C₆H₅—S)-C₆H₄- | 1 | 195–196 (chlorobenzene) |
| 19 | 4-(C₆H₅—SO₂)-C₆H₄- | 1 | 243–244 (acetic acid) |
| 20 | 4-((C₂H₅)₂NSO₂)-C₆H₄- | 1 | 195–196 (butanol) |

-continued

| Example | R | prepared acc. to Example | mp [°C.] (solvent of the recrystallization) |
|---|---|---|---|
| 21 | 3-((CH₃)₂NSO₂)-C₆H₄- | 1 | 219-220 (pentanol) |
| 22 | 3-((C₂H₅)₂NSO₂)-C₆H₄- | 1 | 166-167 (ethanol) |
| 23 | 3-(CH₃CONH)-C₆H₄- | 1 | 243-244 (propanol) |
| 24 | pyridin-3-yl | 1 | 216-217 (ethanol) |
| 25 | 2-CH₃-C₆H₄-CH₂- | 4 | 164-165 (methanol) |
| 26 | 4-F-C₆H₄-CH₂- | 1 | 163-164 (ethanol) |
| 27 | 3-Cl-C₆H₄-CH₂- | 4 | 164-165 (ethanol) |
| 28 | 4-Cl-C₆H₄-CH₂- | 1 | 165-166 (ethanol) |
| 29 | 2-Br-C₆H₄-CH₂- | 1 | 153-154 (ethanol) |
| 30 | 2,4-Cl₂-C₆H₃-CH₂- | 1 | 180-181 (pentanol) |
| 31 | 4-HO-C₆H₄-CH₂- | 1 | 207-208 (pentanol) |

-continued

| Example | R | prepared acc. to Example | mp [°C.] (solvent of the recrystallization) |
|---|---|---|---|
| 32 | 4-CH₃O-C₆H₄-CH₂- | 5 | 154–155 (ethanol) |
| 33 | 3,4-(CH₃O)₂-C₆H₃-CH₂- | 4 | 163–164 (acetic acid) |
| 34 | 2-HO-C₆H₄-CH₂- | 1 | 161–162 (ethanol) |
| 35 | 2-CH₃O-C₆H₄-CH₂- | 5 | 117–118 (toluene) |
| 36 | 2,6-Cl₂-C₆H₃-CH₂- | 1 | 227–228 (acetic acid) |
| 37 | 4-O₂N-C₆H₄-CH₂- | 1 | 187–188 (pentanol) |
| 38 | 3,5-(O₂N)₂-2-CH₃O-C₆H₂-CH₂- | 1 | 161–162 (ethanol) |
| 39 | CH₃OCH₂CH₂CH₂— | 4 | 93–94 (toluene) |
| 40 | C₆H₅-SCH₂— | 1 | 131–132 (methanol) |
| 41 | C₆H₅-SO₂CH₂— | 1 | 248–249 (pentanol) |
| 42 | C₆H₅-SO₂NHCH₂CH₂— | 1 | 134–135 (ethanol) |
| 43 | C₆H₅-SO₂N(C₂H₅)CH₂CH₂— | 1 | 150–151 (methanol) |

-continued

| Example | R | prepared acc. to Example | mp [°C.] (solvent of the recrystallization) |
|---|---|---|---|
| 44 | C₆H₅-NHCH₂CH₂— | 1 | 261–262 (γ-butyrolactone) |
| 45 | C₄H₉NHCOCH₂— | 1 | 129–130 (methanol) |
| 46 | (CH₃)₂NCOCH₂— | 1 | 172–173 (pentanol) |
| 47 | CH₃CON(C₂H₅)CH₂CH₂— | 4 | 179–180 (ethanol) |
| 48 | CH₃NHCON(C₂H₅)CH₂CH₂— | 1 | 178–179 (acetic acid) |
| 49 | C₆H₅N(COCH₃)CH₂CH₂— | 1 | 202–203 (pentanol) |
| 50 | C₆H₅N(CONHCH₃)CH₂CH₂— | 1 | 226–227 (acetic acid) |
| 51 | C₆H₅N(COC₆H₅)CH₂CH₂— | 1 | 225–226 (pentanol) |
| 52 | C₆H₁₁N(H)(COCH₃)... CH₃CONCH₂CH₂— (cyclohexyl) | 5 | 192–193 (propanol) |
| 53 | (pyrrolidinyl)NCH₂CH₂— | 4 | 243–244 (ethanol) |
| 54 | phthalimido-NCH₂CH₂— | 1 | 274 (dec.) (N,N-dimethylformamide) |
| 55 | naphthalimido-NCH₂CH₂— | 1 | 285–286 (acetic acid) |

| Example | R | prepared acc. to Example | mp [°C.] (solvent of the recrystallization) |
|---|---|---|---|
| 56 | 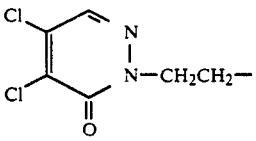 | 1 | 233–234 (pentanol) |

APPLICATION EXAMPLE a) 169 g of 2-cyano-3-amino-3-phenylacrylonitrile were dissolved in 300 ml of N-methylpyrrolidone, 30 g of triethylamine were added, and hydrogen sulfide gas was passed in at 80° C. The gas supply was stopped when the weight had increased by 34 g. The reaction mixture was stirred into 1,000 ml of ice-water and 50 ml of concentrated hydrochloric acid, and the precipitated product was filtered off with suction. Washing with water and drying leaves 180 g of 2-cyano-3-amino-3-phenylacrylic thioamide of the formula

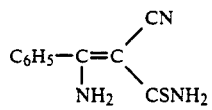

A sample recrystallized from ethanol 217°–218° C. and gives the following analytical values:

| $C_{10}H_9N_3S$ (293) | | | | |
|---|---|---|---|---|
| calculated: | C 59.1 | H 4.5 | N 20.7 | S 15.8 |
| found: | 59.1 | 4.4 | 20.8 | 15.8 | b) 203 g of 2-cyano-3-amino-3-phenylacrylic thioamide were heated to the boil in 1,000 ml of ethanol. 150 g of 30% strength by weight aqueous hydrogen peroxide were added dropwise at such a rate that the reaction mixture remained at the boil for 1 hour without external heating. The reaction mixture was then maintained at the boil for a further 2 hours and thereafter allowed to cool down with stirring. The crystallization was completed by adding 2,000 ml of water. Filtering off with suction, washing and drying left 189 g of 3-phenyl-4-cyano-5-aminoisothiazole having a melting point of 179°–180° C. (from ethanol). Analysis:

| $C_{10}H_7N_3S$ (201) | | | | |
|---|---|---|---|---|
| calculated: | C 59.7 | H 3.5 | N 20.9 | S 15.9 |
| found: | 59.9 | 3.5 | 20.7 | 15.6 |

I claim:
1. A process for preparing a 2-cyano-3-aminoacrylonitrile derivative of the formula I

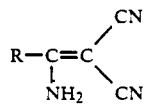

where R is selected from the group consisting of substituted $C_1-C_{10}$-alkyl, styryl or $C_1-C_4$-dialkylamino substituted styryl, phenyl or substituted phenyl and aromatic heterocyclyl, and wherein;

(a) the alkyl substituents are selected from the group consisting of $C_1-C_4$ alkoxy, phenoxy, phenyl or substituted phenyl having a group selected from $C_1-C_4$ alkyl, nitro, halogen and hydroxyl, $C_1-C_4$ alkoxy, $C_1-C_4$-monoalkyl, dialkyl carbamoyl, pyrrolidinocarbonyl, piperidinocarbonyl, morpholinocarbonyl, piperazinocarbonyl, N-($C_1-C_4$-alkyl)piperazinocarbonyl, phenylthio, phenylsulfonyl, anilino, $C_1-C_4$-alkanoylamino, benzoylamino, N-($C_1-C_4$-alkyl)-N-($C_1-C_4$-alkanoyl)-amino, N-($C_5-C_7$-cycloalkyl)-N-($C_1-C_4$-alkanoly)-amino, N-($C_1-C_4$-alkyl)-N-benzoylamino, N-phenyl-N-benzoylamino, phenylsulfamino, N-($C_1-C_4$-alkyl)-phenylsuflonylamino, N-phenyl-N-phenylsulfonylamino, N,N'-($C_1-C_4$-dialkyl)ureido, N-phenyl-N'-($C_1-C_4$-alkyl)ureido, N,N'-diphenylureido, 4,5-dichloropyridazin-1-yl, and a radical taken from the formulas consisting of:

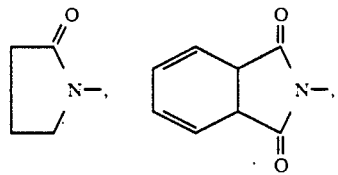

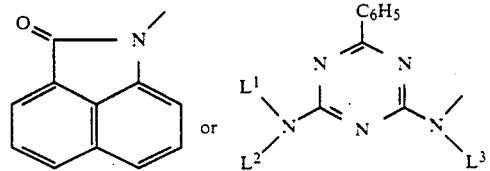

wherein $L^1$, $L^2$ and $L^3$ are identical or different, and each is independent of the others, are hydrogen or $C_1-C_4$-alkyl;

(b) the phenyl substituents are selected from the group consisting of $C_1-C_4$-alkyl, $C_1-C_4$-alkoxy, halogen, hydroxyl, phenoxy, phenylthio, phenylsulfonyl, $C_1-C_4$-alkoxycarbonyl, $C_1-C_4$-hydroxyalkyl, $C_4$-hydroxyalkyl, $C_1-C_4$-haloalkyl, $C_1-C_4$-(pyrrolidino)-, -(piperidino)-, -(morpholino)-, -(piperzino)-, -[N-($C_1-C_4$-alkyl)-piperazino]-alkyl, $C_1-C_4$-phenylalkoxy, $C_1-C_4$-dialkylsulfamoyl and $C_1-C_4$-alkanoylamino;

(c) said aromatic heterocyclyl is selected from the group consisting of pyridinyl, $C_1-C_4$-alkyl substituted pyridinyl, thienyl and $C_1-C_4$ alkyl substituted thienyl; which comprises treating a nitrile of the formula II

R—CN             (II)

where R is as defined above, in an organic diluent at from 0° to 30° C. with a $C_1$–$C_6$ alkanol in the presence of a hydrogen halide and reacting the resulting iminoester hydrohalide of the formula III

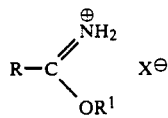

where R is as defined above, $R^1$ is $C_1$–$C_6$-alkyl and X is a halide ion, with or without intermediary isolation, with malodinitrile in an inert organic solvent at from 20 to 100° C. in the presence of a base selected from the group consisting of sodium carbonate, potassium carbonate, sodium bicarbonate, potassium bicarbonate, triethylamine, tripropylamine, triisopropylamine, tributylamine, N,N-dimethylaniline, N,N-diethylaniline, sodium methoxide and sodium ethoxide.

2. A process as claimed in claim 1, wherein the nitrile used is of the formula II where R is 3-($C_1$-$C_4$-alkoxy)-propyl, benzyl or phenyl.

3. A process as claimed in claim 1, wherein the nitrile of the formula II is reacted with methanol, ethanol or propanol and hydrogen chloride.

4. A process as claimed in claim 1 wherein the iminoester hydrohalide of the formula III is further reacted without being isolated first.

* * * * *